United States Patent [19]

Bernstein

[11] Patent Number: 4,735,798

[45] Date of Patent: Apr. 5, 1988

[54] NAILPOLISH REMOVER COMPOSITION

[76] Inventor: Michael Bernstein, 19 Frishman Street, Tel Aviv, Israel

[21] Appl. No.: 775,635

[22] Filed: Sep. 13, 1985

[30] Foreign Application Priority Data

Sep. 13, 1984 [IL] Israel .................................. 72932

[51] Int. Cl.$^4$ ............................................. A61K 7/047
[52] U.S. Cl. ...................................................... 424/61
[58] Field of Search ............................................. 424/61

[56] References Cited

U.S. PATENT DOCUMENTS 3,441,645  4/1969  McKissick et al. .................... 424/61
4,032,464  6/1977  Mausner ............................... 424/61

OTHER PUBLICATIONS

Balsam et al., eds. Cosmetics: Science and Technology p. 568.
The Merck Index, 1976, 9th ed., p. 233.
The CRC Handbook of Data on Organic Compounds, 1985, vol. I, p. 667; and vol. II, pp. 184–185.
The Merck Index, 1983, 10th ed., pp. 644 and 1130–1131.
Chemical Abstracts, 1949, 43:8308h, (R. Fischer et al.).
Dictionary of Solubilities, 1964, Sever and Francis, Cambridge, p. 291.
Dictionary of Organic Compounds, Oxford University Press, New York, 1965, vol. 1: p. 11; vol. 3: pp. 1534–1535; vol. 5: pp. 2781–2782.
B. F. Goodrich Technical Data Sheet No. 57, 1984, The B. F. Goodrich Co., Cleveland, OH 44131.
B. F. Goodrich Technical Bulletin No. GC-67, 1986, B. F. Goodrich, The B. F. Goodrich Co., Cleveland OH 44131.
B. F. Goodrich Bulletin No. PC-1, 1985, B. F. Goodrich Co., The B. F. Goodrich Co., Cleveland, OH 44131.

Primary Examiner—J. R. Brown
Assistant Examiner—Jacqueline M. Stone
Attorney, Agent, or Firm—Merchant, Gould, Smith, Edell, Welter & Schmidt

[57] ABSTRACT

A nailpolish remover composition is disclosed. This composition comprises 30–60% acetone, 10–35% ethyl acetate, 5–20% ethyl alcohol, 5–20% water and 3–15% glycerin, wherein the percentages are on a volume basis, and the ethyl alcohol solubilizes the glycerin in the acetone.

4 Claims, No Drawings

NAILPOLISH REMOVER COMPOSITION

The present invention concerns a novel composition for removing nailpolish.

Nailpolish removers in general are based on acetone. The simplest and least expensive composition contains about 90% acetone and 10% water. Acetone, however, has the undesirable effect of drying out fingernails. Furthermore, acetone penetrates through the skin and is known to be harmful to the liver.

In order to overcome some of the disadvantages of these simple nailpolish remover formulations there have been put on the market compositions containing in addition to acetone, an oil or fatty material. Such compositions contain about 80% acetone, and do not dry out the fingernails. They do, however, have an unpleasant feel and are yellow in color which is not very appealing to women.

There are some expensive commercial nailpolish remover compositions containing in addition to acetone up to three different polyamines and some ethyl acetate. These preparations are also yellow colored.

We have discovered a particularly unique nailpolish remover composition which is water white, has disinfectant properties, strengthens the fingernails, has pleasant feel and makes subsequent coatings of nailpolish adhere better and longer to the fingernails even after dishwashing.

The composition of this invention comprises, on a percent by volume basis:
- 30-60% Acetone
- 10-35% Ethyl acetate
- 5-20% Ethyl alcohol
- 5-20% Water
- 3-15% Glycerin A preferred composition range (percent by volume) is:
- 36-48% Acetone
- 20-30% Ethyl acetate
- 12-18% Ethyl alcohol
- 8-12% Water
- 6-10% Glycerin The acetone, of course, is the major solvent in the composition for removing the nailpolish lacquer.

Ethyl acetate is a stronger and less volatile solvent and is often used in combination with acetone for this purpose.

Ethyl alcohol as such is not a solvent for nailpolish but in the present composition it helps solubilize the glycerin with the acetone. This alcohol may be pure or diluted with water as long as its composition is calculated on a 100% basis.

Glycerin is known to strengthen and lubricate fingernails, but Glycerin is immiscible with acetone.

The water for this composition can come from any source, however, deionized water is preferred. All of these ingredients should of course be of a cosmetically acceptable grade.

A specifically desirable composition of this invention comprises (on a percent by volume basis):
- 46% Acetone
- 23% Ethyl acetate
- 14% Ethyl alcohol
- 10% Water
- 7% Glycerin

We claim:

1. An acetone-based nailpolish remover composition comprising:
   - 36-60% Acetone
   - 10-35% Ethyl acetate
   - 5-20% Ethyl alcohol
   - 5-20% Water
   - 3-15% Glycerin all percentages being on a volume basis; said ethyl alcohol aiding in the solubilization of said glycerin in said acetone; said glycerin being soluble in said acetone; and said nailpolish remover composition being water white.

2. An acetone-based nailpolish remover composition comprising:
   - 36-48% Acetone
   - 20-30% Ethyl acetate
   - 12-18% Ethyl alcohol
   - 8-12% Water
   - 6-10% Glycerin all percentages being on a volume basis; said ethyl alcohol aiding in the solubilization of said glycerin in said acetone; said glycerin being soluble in said acetone; and said nailpolish remover composition being water white.

3. A nailpolish remover composition according to claim 1 comprising:
   - 46% Acetone
   - 23% Ethyl acetate
   - 14% Ethyl alcohol
   - 10% Water
   - 7% Glycerin.

4. A composition in accordance with claim 1, wherein the water is deionized water.

* * * * *